United States Patent [19]

Sugier et al.

[11] Patent Number: 4,529,738
[45] Date of Patent: * Jul. 16, 1985

[54] PROCESS FOR OPERATING HIGHLY EXOTHERMIC REACTIONS

[75] Inventors: André Sugier, Rueil Malmaison; Francois Audibert, Ecully, both of France; Hugo Van Landeghem, deceased, late of Oytier Saint Oblas, France, by Renate Van Landeghem-Heynderickx, legal representative

[73] Assignee: Institut Francais du Petrole, Rueil-Malmaison, France

[*] Notice: The portion of the term of this patent subsequent to Sep. 13, 2000 has been disclaimed.

[21] Appl. No.: 497,940

[22] Filed: May 25, 1983

Related U.S. Application Data

[63] Continuation-in-part of Ser. No. 324,758, Nov. 25, 1981, Pat. No. 4,413,063.

[30] Foreign Application Priority Data

Nov. 25, 1980 [FR] France ................................ 80 25031

[51] Int. Cl.$^3$ .................... C07C 27/06; C07C 1/04
[52] U.S. Cl. .................................. 518/700; 518/713
[58] Field of Search ............................. 518/700, 713

[56] References Cited

U.S. PATENT DOCUMENTS

| | | | |
|---|---|---|---|
| 3,709,919 | 1/1973 | Magoon et al. | 518/713 |
| 3,758,417 | 9/1973 | Magoon et al. | 518/713 |
| 3,888,896 | 6/1975 | Espino et al. | 518/700 |
| 4,031,123 | 6/1977 | Espino et al. | 518/700 |
| 4,413,063 | 11/1983 | Audibert et al. | 518/700 |

FOREIGN PATENT DOCUMENTS

| | | | |
|---|---|---|---|
| 5492 | 11/1979 | European Pat. Off. | 518/713 |
| 229715 | 2/1925 | United Kingdom | 518/700 |
| 1159035 | 7/1969 | United Kingdom | 518/713 |
| 1286970 | 8/1972 | United Kingdom | 518/713 |
| 2087749 | 6/1982 | United Kingdom | 518/700 |

*Primary Examiner*—Howard T. Mars
*Attorney, Agent, or Firm*—Millen & White

[57] ABSTRACT

Improved process for manufacturing methanol by reacting carbon monoxide and/or carbon dioxide with hydrogen. The reactant gases circulate downwardly in admixture with a liquid phase of inert diluent through a methanol synthesis fixed bed catalyst. The superficial velocities of the gas phase and of the liquid phase are at least 1.5 cm per second, under the reaction conditions.

12 Claims, 1 Drawing Figure

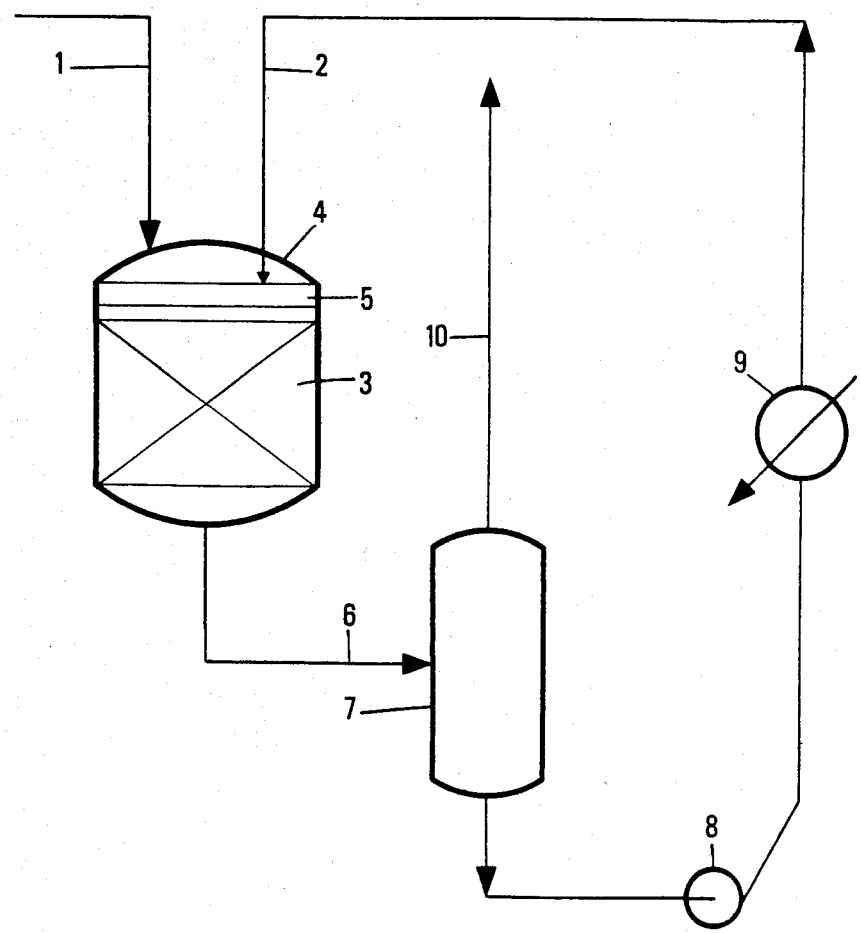

PROCESS FOR OPERATING HIGHLY EXOTHERMIC REACTIONS

STATUS OF THE APPLICATION

This application is a continuation-in-part of our prior application Ser. No. 324,758, filed Nov. 25, 1981, now U.S. Pat. No. 4,413,063.

BACKGROUND OF THE INVENTION

The present invention relates to the synthesis of methanol, a fast and strongly exothermic catalytic reaction, according to the reactions:

$$CO + 2H_2 \rightleftharpoons CH_3OH$$

and/or $$CO_2 + 3H_2 \rightleftharpoons CH_3OH + H_2O.$$

These reactions are so strongly exothermic that in most cases they require the use of a diluent, associated or not with a thermal exchange through the wall of the reactor. Several processes have been designed which make use, as diluent, either of the output gaseous mixture which is then partially recycled, or of a liquid, for example a hydrocarbon, which, under the operating conditions, can remove the heat by direct heat exchange and evaporation.

In the processes operated with a liquid, the catalyst is normally used as a suspension of fine particles, as a fixed bed or as an ebullated bed.

It is important that the catalyst be immersed in the liquid to ensure a good liquid-solid contact everywhere, thereby avoiding the formation of a dry zone in the reactor, which zone could be responsible for an insufficient thermal stability; very high temperatures can be attained in that dry zone, since the reaction can take place entirely in the gas phase therein. A number of techniques have been proposed, wherein a continuous liquid phase is circulated upwardly, the catalyst being used as a suspension, as an ebullated bed or as a fixed or moving bed. These techniques have however serious disadvantages: substantial attrition of the catalyst takes place, due to the displacement of the catalyst particles, even with a so-called fixed bed; fine catalyst particles can be carried away from the reaction zone, resulting in racing of the reaction in the separators, the exchangers or at any other part of the plant.

Although the synthesis of methanol has been disclosed in the prior art (see, for example, U.S. Pat. No. 2,535,060 and U.S. Pat. No. 4,031,123), it has not been appreciated that fixed bed operations could be improved by operating at high velocities of the gas phase and of the liquid phase.

Thermal instability can be sometimes tolerated by the catalyst for a certain time, when it is weak. However it unavoidably results in a shortening of the catalyst life, and a decrease in both activity and selectivity to methanol.

OBJECTS OF THE INVENTION

One object of the present invention is to provide a process which obviates the disadvantages of both processes with a liquid upflow stream and a liquid downflow stream. For example, the following results are obtained:

heat stability of the reactor, resulting in an extended life of the catalyst,
absence of catalyst displacement, resulting in negligible attrition and formation of fines, and
no carrying away of fine particles of catalyst from the reaction zone.

SUMMARY OF THE INVENTION

The present process comprises downwardly circulating the gaseous reactants and a liquid phase of diluent through a fixed bed of catalyst, the superficial velocities of both the gas phase and the liquid phase being at least 1.5 cm/s and more preferably 3-20 cm/s.

BRIEF DESCRIPTION OF THE DRAWING

The FIGURE schematically illustrates an embodiment of the invention.

DETAILED DESCRIPTION OF THE INVENTION

Superficial velocity is intended to mean the ratio of the volumic flow rate of the liquid or gas phase, under the temperature and pressure conditions selected for the reaction, to the reactor cross-section, the latter being considered free of catalyst.

Although the mechanism of the invention is not fully understood, it seems that the flow of gas and liquid is of a different type than observed for lower circulation velocities, for example those conventionally used in the hydrotreatment of hydrocarbons.

The optimum superficial velocity depends in part on the size of the catalyst particles and the physico-chemical properties of the liquid. It seems however practically independent of the superficial velocity of the gas.

The catalyst particles have usefully an average diameter of 1 to 6 mm and preferably 1.5 to 3 mm.

The catalyst is any catalyst known to be effective for the contemplated reaction.

A suitable catalyst consists of a mixture of 10–70 wt percent copper oxide, 15–60 wt percent zinc oxide and 6–40 wt percent aluminum oxide. A preferred one consists of a mixture of 10–60 wt percent copper oxide, 15–50 wt percent zinc oxide, 6–35 wt percent aluminum oxide and 0.5–20 wt percent of at least one oxide of the group formed by the rare earth metal oxides (atomic numbers 57 to 71 inclusive) and/or thorium.

A most preferred catalyst consists of a mixture of 10–60 wt percent copper oxide, 15–50 wt percent zinc oxide, 6–35 wt percent aluminum oxide, 0.5–20 wt percent of at least one oxide selected from the group formed by the rare earth metal oxides (atomic numbers 57 to 71 inclusive) and/or thorium, and 0.05–5 wt percent of at least one metal of the following list: silver, palladium, platinum.

The catalyst can be supported or not. Examples of carriers are silica, alumina, silica-alumina, aluminates, thoria, zirconia, magnesia, silicon carbide, titanium oxide, carbon or metallic carriers, for example as plates or filaments. A preferred carrier is an aluminous cement.

The preferred catalysts (bulk catalysts or supported catalysts) are in the form of balls or of hollow tablets; their average crushing strength (grain to grain) is usefully at least 1 kg/mm for extrudates, at least 2 kg/ball for the balls and at least 50 kg/cm$^2$ (axial crushing strength) for the tablets.

The diluent is a liquid which, under the reaction conditions, does not substantially take part in the reaction and has no detrimental effect on the latter. It is preferably a paraffinic, cycloparaffinic or olefinic hydrocarbon or hydrocarbon fraction (an oil cut) having from 10 up to 30 carbon atoms, for example a gas oil fraction, a fuel oil fraction, a molten paraffin wax, an aromatic oil, a silicone oil, a perfluoroparaffin, a liquid tetrafluorethylene polymer, a heavy alcohol or a mixture of heavy alcohols having, for example, from 10 to 20 carbon atoms, or a permethylated polyethylene glycol.

If the catalyst is affected by sulfur, a previously desulfurized hydrocarbon fraction is preferably used. The sulfur content thereof is usefully less than 100 mg/kg, preferably less than 10 mg/kg and more preferably less than 2 mg/kg.

The so-obtained liquids have usually a density of 0.4 to 2 g/cm$^3$ and a viscosity of 0.05 to 10 centipoises (0.05 to 10 mPa.s) under the conditions of the reaction, these values being illustrative and not mandatory.

Although the stoichiometrical proportions for the reaction are 2 moles of $H_2$ per mole of CO or 3 moles of $H_2$ per mole of $CO_2$, other ratios can be used. For example, when working with a hydrogen deficit, the water formed can react with excess carbon monoxide to generate hydrogen, according to the well-known reaction $$CO + H_2O \rightleftharpoons CO_2 + H_2$$

The $$\frac{H_2}{2CO + 3CO_2}$$

ratio, where $H_2$, CO and $CO_2$ are given as moles, is usefully from 0.5 to 5, preferably from 0.6 to 1.2.

When working with gas recycle, it is preferred that the partial $CO_2$ pressure in the fresh gas be between 0.03 and 1.5 MPa, preferably between 0.08 and 1.2 MPa.

The hourly space velocity by volume is usefully from 1000 to 20,000, preferably from 2,500 to 12,000 for the gas, and from 35 to 700 and preferably from 50 to 300 for the liquid.

The best results of the process are obtained with a good liquid distribution at the top of the reactor obtained by means of devices well known in the art and whose choice is not part of the invention. By way of example, a spraying device can be used, or a distribution plate in strictly horizontal position with a relatively high number of perforations.

The temperatures are usually between 200° and 300° C., preferably between 230° and 280° C., and the pressures are between 3 and 15 MPa preferably between 4 and 12 MPa.

In the FIGURE, a synthesis gas (duct 1) and a liquid phase (duct 2) are circulated downwardly through a methanol synthesis catalyst (3) arranged as a fixed bed in a reactor (4). The liquid is uniformly distributed through a perforated plate (5). The effluent is discharged through duct (6). The liquid phase is separated from the gas phase, at the outlet of the reactor, in the separator (7) and continuously re-circulated by pump (8), through the cooling exchanger (9) and line 2. A fraction of the gas (not shown) can be re-circulated; the effluent gas is discharged through line 10 and analyzed. It can be subjected to condensation to collect the formed products.

EXAMPLE 1

The reactor has a diameter of 3.6 cm (i.d.) and a height of 3.0 m; it contains 1.4 kg (1.0 l) of a catalyst of the formula ($CuO:57.4Al_2O_3:7.36La_2O_3:11.76 ZnO:23.49$ wt %) as balls of 2–2.4 mm, arranged as a fixed bed (depth = 0.98 m).

This catalyst has a filling density of 1.4 kg/l, a porosity of 20 ml/100 g (including 6 ml of macroporous volume above $0.1\mu$). The average diameter of the micropores (those smaller than $0.1\mu$) is 12 nm. The specific surface is 120 m$^2$g$^{-1}$ (BET method). The average crushing strength of the balls (Instroem machine) is 3.2 kg per ball.

The reactor is fed with 5.44 m$^3$/h of a synthesis gas comprising: 66% $H_2$, 28.7% CO, 2.9% $CO_2$ $$\left( \frac{H_2}{2CO + 3CO_2} = 1 \right)$$

GHSV = 5440 h$^{-1}$; it comprises 3.24 m$^3$/h of methanol-free recycle gas and 2.2 m$^3$/h of feed gas. The reactor is also fed with 100 l/h (LHSV = 100 h$^{-1}$) of a $C_{10}$–$C_{18}$ paraffinic fraction (d = 0.769 at 20° C.; viscosity = 0.4 cSt at 250° C.).

Gas and liquid are circulated downwardly.

The initial temperature is 240° C. and the pressure 8 MPa. Under these conditions, the superficial velocity is 3.3 cm/s for the gas and 3.4 cm/s for the liquid; the partial pressure of $CO_2$ in the feed gas is 0.23 MPa.

The $CO_2$ conversion is higher than 74% and the CO conversion is about 97%. The hourly methanol production is about 0.6 kg per liter of catalyst.

The detailed results are the following:

| Time (h) | 500 | 1000 | 8000 |
|---|---|---|---|
| Reactor temperature | 240 | 243 | 245 |
| Pressure drop increase referred to the nominal one (%) | 2% | 5% | 8% |
| Methanol productivity (kg · l$^{-1}$ · h$^{-1}$) | 0.58 | 0.63 | 0.62 |
| $\frac{\text{Methanol produced}}{(CO + CO_2)_{fresh\ gas} - (CO + CO_2)_{purge\ gas}}$ (by mole) | 0.99 | 0.98 | 0.99 |

The resultant methanol, when made free of accompanying water, has a purity higher than 99.5%.

EXAMPLE 2

The new reactor used has a diameter of 5.35 cm (i.d.) and a height of 1.5 m. One liter of the catalyst of example 1 is used (depth of bed: 0.445 m). The feed rate of the synthesis gas as well as the one of the liquid phase are the same as for example 1.

The temperature and pressure of operation are respectively 240° C. and 8.0 MPa.

The superficial gas velocity is 1.5 cm/s and the superficial liquid velocity is 1.54 cm/s.

Detailed results are as follows:

| Time (h) | 500 | 1000 | 8000 |
|---|---|---|---|
| Reactor temperature (°C.) | 240 | 245 | 249 |
| Methanol productivity (KG · l$^{-1}$ · h$^{-1}$) | 0.58 | 0.63 | 0.61 |

| | | | |
|---|---|---|---|
| $\dfrac{\text{methanol produced}}{(CO + CO_2)_{fresh\,gas} - (CO + CO_2)_{purge\,gas}}$ (by mole) | 0.985 | 0.98 | 0.985 |

EXAMPLE 3
(Comparison)

The new reactor used has a diameter of 6.72 cm (i.d.) and a height of 1.0 m. One liter of the catalyst of example 1 is used (depth of bed: 0.282 m). The feed rates for the gas and liquid phases are the same as for examples 1 and 2, as well as reaction temperature and pressure.

The superficial gas velocity is 0.95 cm/s and the superficial liquid velocity is 0.98 cm/s.

Some increases of the temperature of catalyst bed are noticed during this run; they are probably due to an insufficient, homogenity of liquid-gas emulsion close to the catalyst particles. A lower productivity and the formation of some impurities (dimethylether, esters, methane) are noticed, with a corresponding decrease of selectivity to methanol.

Detailed results are as follows:

| Time (h) | 100 | 500 | 1000 | 1500 |
|---|---|---|---|---|
| Reactor temperature (°C.) | 240 | 250 | 255 | 260 |
| Methanol productivity (KG·l$^{-1}$·h$^{-1}$) | 0.51 | 0.50 | 0.49 | 0.48 |
| $\dfrac{\text{methanol produced}}{(CO + CO_2)_{fresh\,gas} - (CO + CO_2)_{purge\,gas}}$ (by mole) | 0.970 | 0.960 | 0.955 | 0.950 |

What is claimed is:

1. In a process for synthesizing methanol, comprising reacting hydrogen with carbon monoxide, carbon dioxide, or a mixture thereof, in the presence of a catalyst for synthesis of methanol, and in the presence of an inert liquid diluent, the improvement comprising downwardly flowing the oxide or oxides of carbon and said hydrogen, as a gas phase, in admixture with a liquid phase of said inert diluent, through a reaction zone comprising a fixed bed of solid particles of said catalyst, at a temperature of 200°-300° C., under a pressure of 3-15 MPa, said particles having an average diameter of 1-6 mm, the superficial velocities of the gas phase and of the liquid phase each being at least 1.5 centimeter per second under the temperature and pressure conditions of the reaction, and the molar ratio $$\dfrac{H_2}{2CO + 3CO_2}$$

being 0.5-5.

2. A process according to claim 1, wherein the hourly space velocity of said gas phase is 1000-20,000.

3. A process according to claim 1, wherein the superficial velocities are both between 3 and 20 cm/s, the reaction temperature is 230°-280° C., the reaction pressure is 4-12 MPa, the catalyst particles have an average diameter of 1.5-3 mm, the molar ratio $$\dfrac{H_2}{2CO + 3CO_2}$$

is 0.6-1.2, the liquid hourly space velocity is 50-300 and the gas hourly space velocity is 2,500'12,000.

4. A process according to claim 1, wherein the superficial velocities are both between 3 and 20 cm/s.

5. A process according to claim 1, wherein the inert diluent has a density of 0.4 to 2 g/cm$^3$ and a viscosity of 0.05 to 10 MPa.s in the reaction conditions.

6. A process according to claim 1, wherein the inert diluent is a hydrocarbon or a hydrocarbon fraction.

7. A process according to claim 1, wherein the inert diluent is a heavy alcohol or a mixture of heavy alcohols.

8. A process according to claim 1, wherein the catalyst particles have an average diameter of 1.5 to 3 mm, said particles being balls of mechanical strength of at least 3 kg/ball.

9. A process according to claim 1, wherein the catalyst comprises, by weight, 10-70% copper oxide, 15-60% zinc oxide and 6-40% aluminum oxide.

10. A process according to claim 1, wherein the catalyst comprises, by weight, 10-60% copper oxide, 15-50% zinc oxide, 6-35% aluminum oxide and 0.5-20% of at least one oxide of a rare earth element or of thorium.

11. A process according to claim 1, wherein the catalyst comprises, by weight, 10-65% copper oxide, 15-50% zinc oxide, 6-35% aluminum oxide, 0.5-20% of at least one oxide or a rare earth element or of thorium and 0.05-5% of at least one metal selected from silver, palladium and platinum.

12. A process according to claim 1, wherein the effluent gas is at least partly recycled and fresh gas is added, said fresh gas having a partial pressure of carbon dioxide of 0.03-1.5 MPa.

* * * * *